US011285319B1

(12) United States Patent
Hubbard et al.

(10) Patent No.: US 11,285,319 B1
(45) Date of Patent: Mar. 29, 2022

(54) METHOD AND SYSTEM FOR IMPROVING QUALITY OF LIFE FOR THE ELDERLY THROUGH NEUROSTIMULATION

(71) Applicant: HRL Laboratories, LLC, Malibu, CA (US)

(72) Inventors: Ryan J. Hubbard, Woodland Hills, CA (US); Praveen K. Pilly, West Hills, CA (US)

(73) Assignee: HRL Laboratories, LLC, Malibu, CA (US)

( * ) Notice: Subject to any disclaimer, the term of this patent is extended or adjusted under 35 U.S.C. 154(b) by 330 days.

(21) Appl. No.: 16/375,593

(22) Filed: Apr. 4, 2019

Related U.S. Application Data

(63) Continuation-in-part of application No. 15/947,733, filed on Apr. 6, 2018, now Pat. No. 10,413,724.

(60) Provisional application No. 62/755,990, filed on Nov. 5, 2018.

(51) Int. Cl.
| | | |
|---|---|---|
| *A61N 1/36* | (2006.01) | |
| *A61B 5/00* | (2006.01) | |
| *A61N 1/04* | (2006.01) | |
| *A61B 5/0205* | (2006.01) | |
| *A61B 5/369* | (2021.01) | |

(Continued)

(52) U.S. Cl.
CPC ........ *A61N 1/36025* (2013.01); *A61B 5/0205* (2013.01); *A61B 5/369* (2021.01); *A61B 5/4812* (2013.01); *A61B 5/6803* (2013.01); *A61B 5/7475* (2013.01); *A61N 1/0456* (2013.01); *A61N 1/36031* (2017.08); *A61B 5/024* (2013.01); *A61B 5/0816* (2013.01)

(58) Field of Classification Search
CPC .... A61N 1/3603; A61N 1/0456; A61B 5/291; A61B 5/7475; A61B 5/4809; A61B 5/6814; G06F 9/542; G09B 19/06
See application file for complete search history.

(56) References Cited

U.S. PATENT DOCUMENTS

| | | |
|---|---|---|
| 5,010,495 A | 4/1991 | Willetts |
| 6,435,876 B1 | 8/2002 | Chen |
| 6,751,505 B1 | 6/2004 | Van Den Honert |

(Continued)

FOREIGN PATENT DOCUMENTS

| | | |
|---|---|---|
| EP | 2409641 | 1/2012 |
| WO | 2016-182947 | 11/2016 |

OTHER PUBLICATIONS

U.S. Appl. No. 16/375,598, filed Apr. 4, 2019, Choe.

(Continued)

*Primary Examiner* — Rex R Holmes
(74) *Attorney, Agent, or Firm* — Ladas & Parry (57) ABSTRACT

A neuro-stimulation system comprising a user interface arranged for providing a user with a series of sensory stimuli, and for selecting, in response to a user input a group of selected sensory stimuli out of said series of sensory stimuli; a non-invasive brain stimulator arranged for stimulating the brain of the user with a different, unique, associated brain stimulus each time the user interface selects one stimulus of said group of selected sensory stimuli; and a controller arranged for detecting slow-wave sleep of the user and for causing the stimulator to stimulate the brain of the user with the brain stimuli associated with said group of selected sensory stimuli during the slow-wave sleep of the user.

24 Claims, 6 Drawing Sheets

(51) Int. Cl.
  *A61B 5/08* (2006.01)
  *A61B 5/024* (2006.01)

(56) References Cited

U.S. PATENT DOCUMENTS

| | | | |
|---|---|---|---|
| 7,052,277 B2 | 5/2006 | Kellman | |
| 7,153,139 B2 | 12/2006 | Wen et al. | |
| 9,149,599 B2 | 10/2015 | Walter | |
| 10,307,592 B1 | 6/2019 | Pilly | |
| 10,413,724 B2 | 9/2019 | Choe | |
| 2003/0225340 A1 | 12/2003 | Collura | |
| 2006/0041242 A1 | 2/2006 | Stypulkowski | |
| 2006/0073452 A1 | 4/2006 | Merzenich | |
| 2006/0212090 A1 | 9/2006 | Lozano | |
| 2007/0060974 A1 | 3/2007 | Lozano | |
| 2007/0213786 A1 | 9/2007 | Sackellares | |
| 2009/0099623 A1 | 4/2009 | Bentwich | |
| 2011/0118534 A1 | 5/2011 | Baror | |
| 2011/0159467 A1 | 6/2011 | Peot | |
| 2011/0288610 A1 | 11/2011 | Brocke | |
| 2012/0184870 A1 | 7/2012 | Shaw | |
| 2013/0011817 A1 | 1/2013 | Cohen Kadosh | |
| 2013/0066392 A1 | 3/2013 | Simon | |
| 2013/0225953 A1 | 8/2013 | Oliviero | |
| 2013/0288223 A1 | 10/2013 | Watterson | |
| 2013/0338738 A1 | 12/2013 | Garcia Molina | |
| 2014/0038147 A1 | 2/2014 | Morrow | |
| 2014/0288614 A1 | 5/2014 | Hagedorn | |
| 2014/0257073 A1* | 9/2014 | Machon | A61B 5/6819 600/383 |
| 2014/0275926 A1 | 9/2014 | Scott et al. | |
| 2015/0050623 A1 | 2/2015 | Falash | |
| 2015/0066104 A1 | 3/2015 | Wingeier | |
| 2015/0079560 A1 | 3/2015 | Cowan | |
| 2015/0105837 A1 | 4/2015 | Aguilar Domingo | |
| 2015/0174418 A1 | 6/2015 | Tyler | |
| 2015/0238762 A1 | 8/2015 | Pal | |
| 2015/0294074 A1 | 10/2015 | Kawato | |
| 2016/0206871 A1 | 7/2016 | Weisend | |
| 2016/0256691 A1 | 9/2016 | Cecchi | |
| 2017/0043167 A1 | 2/2017 | Widge | |
| 2017/0224990 A1* | 8/2017 | Goldwasser | A61N 1/0456 |
| 2017/0249853 A1 | 8/2017 | Weiss | |
| 2017/0304623 A1 | 10/2017 | Tandon | |
| 2017/0368348 A1* | 12/2017 | Le Van Quyen | A61B 5/6803 |
| 2018/0169411 A1* | 6/2018 | Goodall | A61N 1/0541 |
| 2018/0221644 A1 | 8/2018 | Grill | |
| 2020/0139113 A1* | 5/2020 | Shin | A61N 1/0456 |

OTHER PUBLICATIONS

U.S. Appl. No. 15/332,787, filed Oct. 24, 2016, Pilly.
U.S. Appl. No. 15/947,733, filed Apr. 6, 2018, Choe.
From U.S. Appl. No. 15/947,733 (now U.S. Pat. No. 10,413,724), Notice of Allowance dated May 8, 2019.
From U.S. Appl. No. 15/947,733 (now U.S. Pat. No. 10,413,724), Office Action dated Feb. 1, 2019.
Acheson, D. J., et al. "A common neural substrate for language production and verbal working memory," Journal of Cognitive Neuroscience, 23(6), pp. 1358-1367. (2011).
Anderson, J. R., "Cognitive skills and their acquisition," Psychology Press, pp. 143-146 and pp. 243-249, (1981).
Apoorvagiri, N., "Mental Stress and its Implications on Reaction time," International Journal of Computer Trends and Technology, May 2013, pp. 1426 to 1430.
Bates, E., et al. "Functionalism and the competition model," The crosslinguistic study of sentence processing, 3, pp. 73-112. (1989), 60 pages.
Beckner, C., et al., "Language is a complex adaptive system: Position paper," Language Learning, 59(s1), 1-26 (2009).
Berényii, A., et al. "Closed-loop control of epilepsy by transcranial electrical stimulation" Science, vol. 337(6095), 735-737, (2012).

Bikson, M., et al., "Neuroscience: transcranial devices are not playthings," Nature, vol. 501(7466), 167-167, (2013).
Brincat S.L., et al., "Frequency-specific hippocampal-prefrontal interactions during associative learning," Nature Neuroscience, Apr. 2015; vol. 18, No. 4, pp. 576-581. (10 pages).
Brunoni, A. R., et al., "Clinical research with transcranial direct current stimulation (tDCS): challenges and future directions," Brain stimulation, 5(3), 175-195, (2012).
Buckner, R. L., "Memory and executive function in aging and AD: multiple factors that cause decline and reserve factors that compensate," Neuron, vol. 44(1), 195-208, 2004.
Carpenter, J. S., "Psychometric evaluation of the Pittsburgh sleep quality index," Journal of Psychosomatic Research, vol. 45, No. 1, pp. 5-13, 1998.
Choe, J., et al., "Transcranial direct current stimulation modulates neuronal activity and learning in pilot training," Frontiers in human neuroscience, vol. 10, (25 pages) (2016).
Christoff, Joseph A., "Foreign Languages: Human Capital Approach Needed to Correct Staffing & Proficiency Shortfalls," 2002, 56 pages.
Clark, V. P., et al. "TDCS guided using fMRI significantly accelerates learning to identify concealed objects," Neuroimage, 59(1), 117-128, (2012).
Cox, R., et al., "Sound asleep: processing and retention of slow oscillation phase-targeted stimuli," PLOS One, vol. 9, Issue 7, e101567. (2014), pp. 1-12.
Creutzfeldt O.D., et al., "Influence of transcortical d-c currents on cortical neuronal activity," Experimental Neurology, Jun. 1962; 5: pp. 436-452.
DeKeyser, R. M., "What makes learning second-language grammar difficult? A review of issues," Language learning, 55(S1), 1-25 (2005).
DeKeyser, R., "Beyond focus on form: Cognitive perspectives on learning and practicing second language grammar," Focus on form in classroom second language acquisition, 42-63 (1998).
Diekelmann S, et al., "Offline consolidation of memory varies with time in slow wave sleep and can be accelerated by cuing memory reactivations," Neurobiology Learn and Memory, Sep. 2012; 98(2): pp. 103-111.
Dijk, D. J., "Regulation and functional correlates of slow wave sleep," Journal of Clinical Sleep Medicine, vol. 5 (No. 2 Suppl), S6-S15, 2009.
Ferrucci, R., et al., "Transcranial direct current stimulation improves recognition memory in Alzheimer disease," Neurology, 71(7), 493-498, (2008).
Flöel, A., et al., "Noninvasive brain stimulation improves language learning," Journal of Cognitive Neuroscience, 20(8), 1415-1422, (2008).
Fregni, F., et al., "Anodal transcranial direct current stimulation of prefrontal cortex enhances working memory," Experimental brain research, 166(1), pp. 23-30. (2005).
Frohlich F, et al., "Endogenous electric fields may guide neocortical network activity," Neuron, Jul. 15, 2010; 67(1): pp. 129-143.
Gais, S, et al., "Low acetylcholine during slow-wave sleep is critical for declarative memory consolidation," Proceedings of National Academy of Sciences of USA, Feb. 17, 2004; 101(7): pp. 2140-2144.
Galvez-García, G., et al. "Mitigating Simulator Adaptation Syndrome by means of tactile stimulation," Applied Ergonomics, 58, 13-17. (2017).
Gerrard, J. L., "Sequence reactivation in the hippocampus is impaired in aged rats," Journal of Neuroscience, 28(31), 7883-7890, 2008.
Hodges, S., "SenseCam: A wearable camera that stimulates and rehabilitates autobiographical memory," Memory, 19(7), 685-696, 2011 (18 pages).
Jacobson, L., et al. "tDCS polarity effects in motor and cognitive domains: a meta-analytical review," Experimental brain research, 216(1), 1-10. (2012).
Ji, D, et al., "Coordinated memory replay in the visual cortex and hippocampus during sleep," Nature Neuroscience. 2007, vol. 10(1): pp. 100-107.

(56) References Cited

OTHER PUBLICATIONS

Jutras MJ, et al., "Oscillatory activity in the monkey hippocampus during visual exploration and memoiy formation," Proceedings of National Academy of Sciences, Aug. 6, 2013, vol. 110, No. 32, pp. 13144-13149.

Kali S, et al., "Off-line replay maintains declarative memories in a model of hippocampal-neocortical interactions," Nature Neuroscience, 2004, vol. 7, No. 3, pp. 286-294.

Kirov R, et al., "Slow oscillation electrical brain stimulation during waking promotes EEG theta activity and memory encoding," Proceedings of National Academy of Sciences. 2009, vol. 106, pp. 15460-15465.

Krause, M. R., et al., "Transcranial Direct Current Stimulation Facilitates Associative Learning and Alters Functional Connectivity in the Primate Brain," Current Biology, 27(20), 3086-3096 (2017), 15 pages.

Lim, A. S., "Sleep fragmentation and the risk of incident Alzheimer's disease and cognitive decline in older persons," Sleep, vol. 36 No. 7, 1027-1032, 2013 (8 pages).

Little, S, et al. "Adaptive deep brain stimulation in advanced Parkinson disease," Annals of Neurology, 2013, 74:449-457.

Liu, M., et al., "A look at the research on computer-based technology use in second language learning: A review of the literature from 1990-2000," Journal of Research on Technology in Education, 34(3), 54 pages (2002).

Manenti, R., "Enhancing verbal episodic memory in older and young subjects after non-invasive brain stimulation," Frontiers in Aging Neuroscience, vol. 5, 2013 (9 pages).

Marshall, L., "Boosting slow oscillations during sleep potentiates memory," Nature, vol. 444(7119), pp. 610-613, 2006.

McNamara C.G., et al., "Dopaminergic neurons promote hippocampal reactivation and spatial memory persistence," Nature Neuroscience, 2014, vol. 17, No. 12 pp. 1658-1660.

Merzagora, Anna C., et al., "Prefrontal hemodynamic changes produced by anodal direct current stimulation." Neuroimage 49, No. 3 (2010): pp. 2304-2310.

Minichino, A., "Prefronto-cerebellar transcranial direct current stimulation improves sleep quality in euthymic bipolar patients: a brief report," Behavioural Neurology, 2014 (3 pages).

Mougeon, R., et al., "The sociolinguistic competence of immersion students," (vol. 47). Multilingual Matters, pp. 48-87, (2010).

Ngo, H., et al. "Driving Sleep Slow Oscillations by Auditory Closed-Loop Stimulation—A Self-Limiting Process," The Journal of Neuroscience, 35(17), 6630-6638. (2015).

Ngo, H., et al., "Auditory closed-loop stimulation of the sleep slow oscillation enhances memory," Neuron, 78(3), pp. 545-553 (2013).

Nitsche, M. A., et al., "Transcranial direct current stimulation: state of the art 2008," Brain stimulation, 1(3), 206-223, (2008).

Operation and Maintenance Overview, Fiscal Year 2016 Budget Estimates, Feb. 2015, Office of the Under Secretary of Defense (Comptroller) / Chief Financial Officer, p. 13. (282 pages).

Osipova D, et al., "Theta and gamma oscillations predict encoding and retrieval of declarative memory," Journal of Neuroscience, 2006; 26(28): pp. 7523-7531.

Osorio, I, et al. "Automated seizure abatement in humans using electrical stimulation," Ann Neurol 2005, 57:258-268.

Pace-Schott, E. F., "Age-related changes in the cognitive function of sleep," Progress in Brain Research, vol. 191, pp. 75-89, 2011.

Pienemann, Manfred (Editor), "Similarities and differences in L1 and L2 development. Opening up the perspective," by Gisela Hakansson, An introduction to processability theory. Cross-linguistic aspects of processability theory, 30, pp. 179-199. (2005).

Potowski, K., et al., "The effects of instruction on linguistic development in Spanish heritage language speakers," Language Learning, 59(3), 537-579, (2009).

Rasch B, et al, "Odor cues during slow-wave sleep prompt declarative memory consolidation," Science. 2007; 315(5817): pp. 1426-1429.

Rasch BH, et al., "Combined blockade of cholinergic receptors shifts the brain from stimulus encoding to memory consolidation," Journal of Cognitive Neuroscience, May 2006; 18(5): pp. 793-802.

Rolls E.T., "Hippocampo-cortical and cortico-cortical backprojections," Hippocampus. 2000; 10: pp. 380-388.

Rudoy J.D., et al., "Strengthening Individual Memories by Reactivating Them During Sleep," Science. Nov. 20, 2009;326(5956): pp. 1079-1079.

Sachdev, P. S., "The prevalence of mild cognitive impairment in diverse geographical and ethnocultural regions: The COSMIC Collaboration," PLOS One, 10(11), e0142388, pp. 1-19, 2015.

Santostasi, G., et al., "Phase-locked loop for precisely timed acoustic stimulation during sleep," Journal of Neuroscience Methods, 259, 101-114, (2016).

Schade, C.M., et al., "Automatic adaptation of neurostimulation therapy in response to changes in patient position: results of the Posture Responsive Spinal Cord Stimulation (PRS) Research Study," Pain Physician 2011, 14:407-417.

Schultz, D.M., et al. "Sensor-driven position-adaptive spinal cord stimulation for chronic pain," Pain Physician 2012, 15:1-12.

Schumann, J. H., "Research on the acculturation model for second language acquisition," Journal of multilingual & multicultural development, 7(5), pp. 379-392. (1986).

Sederberg, P.B., et al., "Theta and gamma oscillations during encoding predict subsequent recall," Journal of Neuroscience, Nov. 26, 2003; 23(34): pp. 10809-10814.

Tergau, F., et al. "Low- frequency repetitive transcranial magnetic stimulation improves intractable epilepsy," The Lancet, vol. 353(9171), 2209. (1999).

Van Elmpt W.J., et al. "A model of heart rate changes to detect seizures in severe epilepsy," Seizure (2006),15:366-375.

From U.S. Appl. No. 16/375,598 (unpublished, non-publication request filed), office action dated Apr. 21, 2021.

From U.S. Appl. No. 16/375,598 (unpublished, non-publication request filed), office action dated Jan. 21, 2021.

* cited by examiner

METHOD AND SYSTEM FOR IMPROVING QUALITY OF LIFE FOR THE ELDERLY THROUGH NEUROSTIMULATION

RELATED APPLICATIONS

This application is related to U.S. Pat. No. 10,307,592, filed on Oct. 24, 2016, which is hereby incorporated by reference. This application claims priority of U.S. Pat. No. 10,413,724, filed on Apr. 6, 2018, which is hereby incorporated by reference. This application claims priority of U.S. provisional application No. 62/755,993, filed on Nov. 5, 2018, which is hereby incorporated by reference.

STATEMENT REGARDING FEDERALLY SPONSORED RESEARCH OR DEVELOPMENT

This invention was made with Government support under contract number W911NF-16-C-0018 RAM Replay. The Government has certain rights in the invention.

TECHNICAL FIELD

This presentation relates to a method and system that allow improving quality of life and reducing the risk of developing mild cognitive impairment (MCI) in individuals, in particular elderly, through application of transcranial brain stimulation.

BACKGROUND

Aging leads to impairments in episodic memory function, and MCI exacerbates this memory decline even further [See for example "Memory and executive function in aging and AD: multiple factors that cause decline and reserve factors that compensate", by Buckner, R. L. (2004). Neuron, 44(1), 195-208.]. Additionally, slow-wave sleep, a stage of non-REM sleep (non-Rapid Eye Movement sleep) that has important functions for healthy sleep maintenance and memory consolidation [see for example "Regulation and functional correlates of slow wave sleep", by Dijk, D. J. (2009). Journal of Clinical Sleep Medicine, 5(2 Suppl), S6], is decreased in old age, and further decreased by MCI [see for example "Age-related changes in the cognitive function of sleep", by Pace-Schott, E. F., & Spencer, R. M. (2011); Progress in Brain Research, 191, 75]. Older adults with especially disrupted slow-wave sleep are at higher risk for developing MCI, as well as Alzheimer's disease [see for example "Sleep fragmentation and the risk of incident Alzheimer's disease and cognitive decline in older persons", by Lim, A. S., Kowgier, M., Yu, L., Buchman, A. S., & Bennett, D. A. (2013); Sleep, 36(7), 1027-1032]. Finally, neural replay of previously encoded memories during slow-wave sleep is impaired with age, leading to impaired memory consolidation [see for example "Sequence reactivation in the hippocampus is impaired in aged rats. Journal of Neuroscience", by Gerrard, J. L., Burke, S. N., McNaughton, B. L., & Barnes; C. A. (2008). 28(31), 7883-7890].

A patent application by Goldman, Hardy, Mahncke, Merzenich, & Zimman: US20060073452A1, entitled "Method for enhancing memory and cognition in aging adults" (2005), discloses a computerized task that requires users to discriminate between computer-generated phonemes. The concept here is that adults improve their auditory processing, leading to less noisy sensory representations and increased processing speed. A main disadvantage is that this system does not specifically target episodic memory, sleep disturbances, or memory consolidation.

A patent application by Simon, Errico, & Raffle: US20130066392A1, entitled "Non-invasive magnetic or electrical nerve stimulation to treat or prevent dementia" (2012), discloses a system for treating or preventing MCI and AD based on electrical or magnetic stimulation of the vagus nerve in order to modulate activity of the locus coeruleus, causing release of norepinephrine to counteract neuroinflammation. While this system can potentially reduce the prevalence of MCI, it provides no specific cognitive enhancement or sleep quality improvement. Additionally, it is unclear if this system would be able to function in an automatic, closed-loop, manner, or would require a clinician to operate.

A patent application by Bentwich: US20090099623A1, entitled "Systems and methods for treatment of medical conditions related to the central nervous system and for enhancing cognitive functions" (2008), teaches identifying specific brain regions related to central nervous system disorders or cognitive functions, and targeting them for non-invasive stimulation to treat the disorder or improve the cognitive function.

A patent application by Lozano and Mayberg: US20060212090A1, entitled "Method of treating cognitive disorders using neuromodulation" (2006) discloses surgically implanting an electrode to stimulate a specific site in order to treat a cognitive disorder or enhance a cognitive ability. A primary disadvantage here is the invasiveness of performing surgery to implant an electrode.

A reference by Hodges, S., Berry, E., & Wood, K. (2011) entitled "SenseCam: A wearable camera that stimulates and rehabilitates autobiographical memory". Memory, 19(7), 685-696, discloses a wearable camera system that records events during the participant's daily life. The events can be uploaded to a computer and examined later to improve recall of autobiographical memories.

There remains a need for an easy to use system of neurostimulation that allows to efficiently and conveniently reduce memory deficit.

SUMMARY

In a system according to an embodiment of the present disclosure, an elderly human participant outfitted with neural recording and stimulation devices (e.g., an electroencephalogram (EEG) recording device having also stimulation electrodes) performs a cognitive task designed to alleviate episodic memory impairments, and receives personalized, targeted brain stimulation patterns unique to each episode during episodes of the task in order to strengthen encoding and tag memories for replay during sleep. This cognitive task can cue memories that the user wishes to remember by for example presenting events recorded during the day, which can be automatically determined or selected by the user. The unique brain stimulation patterns are then re-applied during sleep, preferaby following the detection of specific neurophysiological sleep cues, in order to strengthen sleep-mediated consolidation, boost slow-wave sleep, and increase targeted neural replays during sleep. Enhancing slow-wave sleep and neural replay of memories leads to reduced risk of developing dementia, as these are risk factors and biomarkers associated with development of neurodegenerative disease. Finally, embodiments of this presentation can comprise a simple and easy-to-use computerized task, a compact and highly wearable neural recording, stimulation, and video recording ensemble, and a device for automatic monitoring and tracking of sleep biometrics. Such a system can for example allow elderly patients to use it autonomously from their own home.

Embodiments of this presentation relate to a neuro-stimulation system comprising: a user interface arranged for providing a user with a series of sensory stimuli, and for selecting, in response to a user input a group of selected sensory stimuli out of said series of sensory stimuli; a non-invasive brain stimulator arranged for stimulating the brain of the user with a different, unique, associated brain stimulus each time the user interface selects one stimulus of said group of selected sensory stimuli; and a controller arranged for detecting slow-wave sleep of the user and for causing the stimulator to stimulate the brain of the user with the brain stimuli associated with said group of selected sensory stimuli during the slow-wave sleep of the user.

According to embodiments of this presentation, each brain stimulus comprises a non-invasive stimulation to the prefrontal cortex.

According to embodiments of this presentation, each brain stimulus comprises a spatiotemporal amplitude modulated pattern comprising a pattern of electrical stimulations spatially distributed across the scalp, where the stimulations oscillate at a predetermined frequency for a predetermined period of time.

According to embodiments of this presentation, each sensory stimulus comprises a video of events experienced by said user.

According to embodiments of this presentation, said user interface is arranged for measuring said user input by observing predetermined physiological parameters of the user; and said user interface is arranged for selecting said group of selected sensory stimuli in response to said user input by selecting automatically, among said series of provided sensory stimuli, the sensory stimuli in response to which the user interface can sense a user reaction having a value above a predetermined threshold value.

According to embodiments of this presentation, the system further comprises neurophysiological data sensors arranged for detecting predetermined neurophysiological data from the user and sending said data to said controller; wherein said controller is arranged for detecting slow-wave sleep of the user based on an evaluation of the spectral power of said data, wherein the evaluation is performed automatically.

According to embodiments of this presentation, said neurophysiological data sensors are arranged for measuring predetermined biomarkers following each brain stimulus during sleep and wherein said controller is provided for discontinuing the use of any brain stimulus that, when used to stimulate the brain of the user during sleep, does not cause said predetermined biomarkers to change in a desired manner.

According to embodiments of this presentation, said neurophysiological data sensors and said non-invasive brain stimulator are arranged on a headgear adapted to be worn by the user.

According to embodiments of this presentation, said controller is arranged for tracking the user's heart rate and respiration rate, and for additionally stimulating the user's brain with the brain stimuli associated with said group of selected sensory stimuli during periods of restlessness or elevated arousal.

According to embodiments of this presentation, said user interface is arranged for associating a cue to each stimulus of said group of selected sensory stimuli, either automatically or by user input.

According to embodiments of this presentation, said user interface is arranged for, after stimulation of the user's brain during sleep: providing said group of selected sensory stimuli to the user; prompting the user to recognize and enter the cue associated to each stimulus; and recording if said cue is recognized or not by the user.

According to embodiments of this presentation, the neuro-stimulation system comprises neurophysiological data sensors arranged for detecting and recording predetermined neurophysiological data from the user's brain when said user is stimulated by each of said group of brain stimuli; the controller being further arranged for: associating the neurophysiological data recorded for each brain stimuli with the record of the cue of the brain stimuli being recognized or not by the user; providing the user with a further series of sensory stimuli and allowing said user to select a further group of selected sensory stimuli out of said further series of sensory stimuli; having the neurophysiological data sensors detect and record further neurophysiological data from the user's brain when stimulated by each of said further group of brain stimuli; and if the further neurophysiological data, detected when the user's brain is stimulated by at least one stimulus of said further group of brain stimuli, has been associated to a record of the user not recognizing a cue, causing the stimulator to additionally stimulate the brain of the user with said at least one stimulus of said further group of brain stimuli.

According to embodiments of this presentation, said neurophysiological data sensors comprise an electroencephalogram recording device.

Embodiments of this presentation also relate to a method comprising: with a user interface, providing a user with a series of sensory stimuli, and selecting, in response to a user input, a group of selected sensory stimuli out of said series of sensory stimuli; with a non-invasive brain stimulator, stimulating the brain of the user with a different, unique, associated brain stimulus each time the user interface selects one stimulus of said group of selected sensory stimuli; and with a controller, detecting slow-wave sleep of the user and causing the stimulator to stimulate the brain of the user with the brain stimuli associated with said group of selected sensory stimuli during the slow-wave sleep of the user.

According to embodiments of this presentation, each brain stimulus comprises a non-invasive stimulation to the prefrontal cortex.

According to embodiments of this presentation, each brain stimulus comprises a spatiotemporal amplitude modulated pattern that includes a pattern of electrical stimulations spatially distributed across the scalp, where the stimulations oscillate at a predetermined frequency for a predetermined period of time.

According to embodiments of this presentation, each sensory stimulus comprises a video of events experienced by said user.

According to embodiments of this presentation, the method further comprises: with said user interface, measuring said user input by observing predetermined physiological parameters of the user; and with said user interface, selecting said group of selected sensory stimuli in response to said user input by selecting automatically, among said series of provided sensory stimuli, the sensory stimuli in response to which the user interface can sense a user reaction having a value above a predetermined threshold value.

According to embodiments of this presentation, the method further comprises: detecting predetermined neurophysiological data from the user with neurophysiological data sensors; sending said data to said controller; and with said controller, detecting slow-wave sleep of the user based on an evaluation of the spectral power of said data, wherein the evaluation is performed automatically.

According to embodiments of this presentation, the method further comprises: with said neurophysiological data sensors, measuring predetermined biomarkers following each brain stimulus during sleep; and with said controller, discontinuing the use of any brain stimulus that, when used to stimulate the brain of the user during sleep, does not cause said predetermined biomarkers to change.

According to embodiments of this presentation, the method further comprises: with said controller, tracking the user's heart rate and respiration rate, and additionally stimulating the user's brain with the brain stimuli associated with said group of selected sensory stimuli during periods of restlessness or elevated arousal.

According to embodiments of this presentation, the method further comprises: with said user interface, associating a cue to each stimulus of said group of selected sensory stimuli, either automatically or by user input.

According to embodiments of this presentation, the method further comprises: with said user interface and after stimulation of the user's brain during sleep, providing said group of selected sensory stimuli to the user and prompting the user to recognize and enter the cue associated to each stimulus; and recording if said cue is recognized or not by the user.

According to embodiments of this presentation, the method further comprises: with neurophysiological data sensors, detecting and recording predetermined neurophysiological data from the user's brain when the user's brain is stimulated by each brain stimulus of said group of brain stimuli; with said controller, associating the neurophysiological data recorded for each brain stimuli with the record of the cue of said brain stimuli being recognized or not by the user; providing the user with a further series of sensory stimuli and allowing said user to select a further group of selected sensory stimuli out of said further series of sensory stimuli; having said neurophysiological data sensors detect and record further neurophysiological data from the user's brain when stimulated by each of said further group of brain stimuli; and if the further neurophysiological data, detected when the user's brain is stimulated by at least one stimulus of said further group of brain stimuli, has been associated to a record of the user not recognizing a cue, causing the stimulator to additionally stimulate the brain of the user with said at least one stimulus of said further group of brain stimuli.

According to an embodiment of this presentation each sensory stimulus is a video of events experienced by said user. The events may have been recorded shortly (e.g., the same day) before they are submitted to the user for selection. The sensory stimuli can alternatively comprise smells (e.g., from a library of bottled samples), sounds, pictures, text, tastes (e.g., from a library of samples), touch sensation (e.g., from a library of samples), heat sensation, etc.

The user interface can be arranged for allowing the user to select the sensory stimuli by observing physiological parameters of the user, for example an electroencephalogram of the user, and selecting automatically the sensory stimuli in response to which the user interface can sense a user reaction having a value above a predetermined threshold value.

DESCRIPTION

The following description is presented to enable one of ordinary skill in the art to make and use the teachings of this presentation and to incorporate them in the context of particular applications. Various modifications, as well as a variety of uses in different applications will be readily apparent to those skilled in the art, and the general principles defined herein may be applied to a wide range of embodiments. Thus, the invention described in this presentation is not intended to be limited to the embodiments presented, but is to be accorded the widest scope consistent with the principles and novel features disclosed herein.

In the following detailed description, numerous specific details are set forth in order to provide a more thorough understanding of embodiments of this presentation. However, it will be apparent to one skilled in the art that such embodiments may be practiced without necessarily being limited to these specific details.

All the features disclosed in this presentation, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

The Inventors have shown that by applying non-invasive transcranial electrical neurostimulation according to the present disclosure, one can reduce the memory deficits outlined above [see also "*Enhancing verbal episodic memory in older and young subjects after non-invasive brain stimulation*", by Manenti, R., Brambilla, M., Petesi, M., Ferrari, C., & Cotelli, M. (2013); Frontiers in Aging Neuroscience, 5], potentiate slow-wave sleep [see also "*Boosting slow oscillations during sleep potentiates memory*", by Marshall, L., Helgadóttir, H., Mölle, M., & Born, J; (2006). Nature, 444(7119), 610], and improve sleep quality [see also "*Prefronto-cerebellar transcranial direct current stimulation improves sleep quality in euthymic bipolar patients: a brief report*" by Minichino, A., Bersani, F. S., Spagnoli, F., Corrado, A., De Michele, F., Calò, W. K., . . . & Vergnani, L. (2014); Behavioural Neurology, 2014"].

Systems designed at HRL Laboratories and disclosed for example in U.S. application Ser. No. 15/332,787, which is hereby incorporated by reference, allow targeting specific neural replays during slow wave sleep for stimulation, leading to improvement and acceleration of consolidation. By improving sleep and memory reactivation, one can decrease the incidence of MCI, which affects 15-20% of older adults and is associated with higher mortality rates [see for example "*The prevalence of mild cognitive impairment in diverse geographical and ethnocultural regions: The COSMIC Collaboration*" by Sachdev, P. S., Lipnicki, D. M., Kochan, N. A., Crawford, J. D., Thalamuthu, A., Andrews, G., . . . & Katz, M. J. (2015); PloS One, 10(11), e0142388].

Current state-of the art interventions primarily rely on invasive procedures, such as surgery or deep brain stimulation, whereas embodiments of this presentation are non-invasive and can be used from home. Also, while systems may exist to improve one component of the deficits elderly adults face (e.g., memory), systems according to embodiments of this presentation can improve a larger number of components simultaneously. Finally, systems according to embodiments of this presentation can allow users to autonomously interact with the device from their own home. Systems according to embodiments of this presentation can either determine which memories to target automatically through the use of saliency detection of recorded episodes, or can target memories specified by the user.

The purpose of embodiments of this presentation is to improve the quality of life of older adults through a multi-prong approach: improving memory for life events, improving sleep quality, and reducing risk of MCI. The proposed system can for example be used to improve the abilities and increase the output of older workers. As life expectancies grow and birth rates fall, there will be more and more older workers in the workforce. If these workers experience cognitive decline or MCI, they will be less effective at their jobs. By targeting this population for improvement, their employers can stave off potential losses of profit due to failing workers. Additionally, the proposed system has great commercial viability in the marketplace, as the forecasted market size for cognitive assessment and training is 8.06 billion USD by 2021 [see for example: "*Research and Markets*. (2017, April). *Cognitive Assessment and Training Market by Assessment Type (Pen- and Paper-Based, Hosted, Biometrics), Component, Application (Clinical Trial, Screening & Diagnostics, Brain Training, Academic Research), Vertical, & Region*"—Global Forecast to 2021. Available from https://www.researchanelmarkets.com/].

Previous efforts in the field of neurostimulation have relied on manual stimulation without any specificity in time, which reduced the capabilities of the system as well as the potential for the commercialization of the technology. By employing a closed-loop system; i.e., a system capable of automatically identifying biomarkers for determining when to stimulate, the utility and capacity for commercialization of the system is increased. A system with closed-loop sensing and stimulation capability has been previously disclosed by HRL Laboratories' U.S. application Ser. No. 15/947,733, which is hereby incorporated by reference, and this presentation can be considered as related to that technology. Additionally, while brain training products exist in various forms, previous work on enhancing cognition in older adults has not focused specifically on combining episodic memory enhancement with non-invasive neurostimulation for improvement. Thus, a system according to this presentation can provide greater benefits than products currently on the market.

The existing prior art may comprise individual components of embodiments of this presentation in a simplified form, but ultimately lack combining said individual components with important elements that make this presentation unique. For example, prior works on neurostimulation for improving memory, sleep, or treating MCI lack the capacity to personalize stimulation, lack the ability to monitor brain states for maximizing the efficacy of neurostimulative intervention, and do not focus on stimulation of neural replays of memories during slow-wave sleep to maximize consolidation, contrary to what the presently disclosed systems and methods do. This presentation describe a number of features that are essentially not described in the literature, and that have only recently been instantiated through research performed by HRL Laboratories. Furthermore, the application of a closed-loop stimulation technology as detailed in this presentation, for example in conjunction with personalized testing of episodic memories recorded or selected by the user, has not been previously proposed nor has been investigated in the literature.

There has been research, such as the SenseCam [see for example "*SenseCam: A wearable camera that stimulates and rehabilitates autobiographical memory*" by Hodges, S., Berry, E., & Wood, K. (2011); Memory, 19(7), 685-6%], that has focused on recording events that occur throughout the day and using this information as an autobiographical cue to aid retrieval of memories. However, no research to date has combined this real-life event data with neurostimulation, particularly during sleep. Finally, little research has been done on treating MCI through slow-wave potentiation and targeted neurostimulation of specific replays during sleep.

Figure 1:
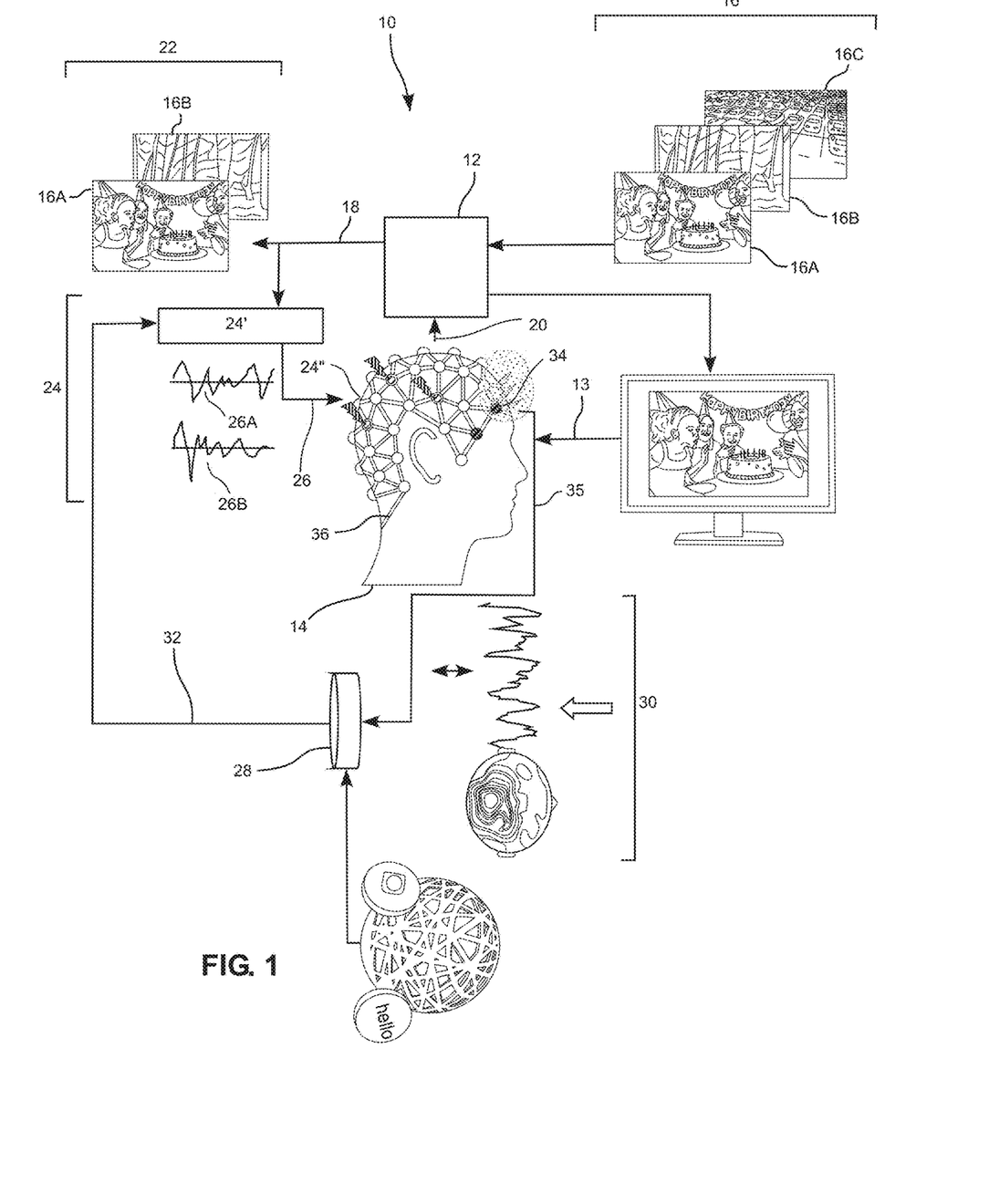
FIG. 1 illustrates a high-level outline of a system according to embodiments of this presentation.

FIG. 1 illustrates a high-level outline of a neuro-stimulation system 10 according to an embodiment of this presentation, comprising: a user interface 12 arranged for providing 13 a user 14 with a series 16 of sensory stimuli (16A, 16B, 16C illustrated) and for selecting 18, in response to a user input 20 a group 22 of selected sensory stimuli (16A, 16B illustrated) out of said series 16 of sensory stimuli. System 10 further comprises a non-invasive brain stimulator 24 (comprising for example a signal generator 24' and electrodes 24") arranged for stimulating 26 the brain of the user 14 with a different, unique, associated brain stimulus (26A, 26B illustrated) each time the user interface 12 selects 18 one stimulus (16A, 16B illustrated) of said group 22 of selected sensory stimuli; and a controller 28 arranged for detecting 30 slow-wave sleep of the user 14 and for causing 32 the stimulator 24 to stimulate the brain of the user 14, with the brain stimuli 26 associated with said group 22 of selected sensory stimuli, during the slow-wave sleep of the user. According to an embodiment of this presentation, the interface 12, the signal generraor 24' and the controller 28 can be dedicated hardware or they can be implemented on a computer by programming.

According to an embodiment of this presentation, each brain stimulus (26A, 26B) comprises a non-invasive stimulation to the prefrontal cortex, and it can comprise a spatiotemporal amplitude modulated pattern comprising a pattern of electrical stimulations spatially distributed across the scalp of the user, where the stimulations oscillate at a predetermined frequency for a predetermined period of time.

According to an embodiment of this presentation, each sensory stimulus (16A, 16B, 16C) comprises a video of events experienced by said user. According to an embodiment of this presentation, system 10 can comprise a camera (wearable or fixed, not shown in FIG. 1) that allows the user to generate the sensory stimuli for example as his day goes by. Three stimuli (16A, 16B, 16C) are illustrated as being presented to the user for selection, and two as selected, but any number of stimuli can be presented to the user, and any lower number of stimuli can be selected by the interface.

The selection of the stimuli 16 by the interface 12 can be automatic. For example, user interface 12 can be arranged for receiving a user input 20 that is generated by observing predetermined physiological parameters of the user; and for selecting automatically 18 the group 22 of selected sensory stimuli (16A, 16B) in response to which the user interface can sense a user reaction having a value above a predetermined threshold value. The selection of the stimuli 16 by the interface can also be manual, for example in response to a user input such as the pressing of a button (not shown) by the user. As detailed hereafter, user 14 can be prompted to press on the button upon indication of a salient user reaction.

According to an embodiment of this presentation, system 10 can comprise neurophysiological data sensors 34 (e.g., electroencephalogram sensors) arranged for detecting predetermined neurophysiological data 35 from the user 14 and sending said data 35 to controller 28; which is arranged for detecting slow-wave sleep of the user based for example on an evaluation of the spectral power of said data, wherein the evaluation is performed automatically. According to an embodiment of this presentation, said predetermined neurophysiological data 35 can comprise electroencephalograpy (EEG), or any other invasive or non-invasive neural recording, such as functional near infrared spectroscopy (fNIRS) and electrocortocography (ECoG). According to an embodiment of this presentation, the neurophysiological data sensors 34, as well as the electrodes 24" of the non-invasive brain stimulator 24 are arranged on a headgear 36, for example adapted to be worn by the user when the user is awake or sleeping. According to an embodiment of this presentation, the neurophysiological data sensors 34, output 35, and the controller 28 can be arranged to detect a salient user reaction and to generate appropriate signals in response, such as user input 20.

According to an embodiment of this presentation, the neurophysiological data sensors 34 are arranged for measuring predetermined biomarkers following each brain stimulus 26 during sleep and the controller 28 is provided for causing stimulator 24 to discontinue the use of any brain stimulus 26 that, when used to stimulate the brain of the user 14 during sleep, does not cause said predetermined biomarkers to change in a desired manner.

According to an embodiment of this presentation, the controller 28 can be arranged for tracking the user's heart rate and respiration rate (for example using heart rate and respiration sensors 38), and can be arranged for additionally stimulating the user's brain with the brain stimuli (26A, 26B) associated with said group (22) of selected sensory stimuli (16A, 16B) during periods of restlessness or elevated arousal of the user 14.

In brief, the system 10 can allow the user 14 to collect episodes (16A, 16B) that they wish to remember with for example a wearable camera device, and to later study/select these episodes while receiving brain stimuli (such as SpatioTemporal Amplitude-Modulated Pattern (STAMP) neurostimulations) to tag the episodes. Next, user 14 sleeps and receives again the brain stimuli received earlier when selecting the episodes, to cue reactivation of memories and boost slow-wave amplitude. It is noted that the user can test his memory and his sleep quality to ensure the system is improving well-being.

An important aspect of improving quality of life for the elderly, as well as reducing MCI risk, is improving their memory for personal life events, or episodes. Thus, a system according to embodiments of this presentation preferably comprises a collection of memories/episodes from the user that can be cued for reactivation later. Alternatively, the user can be asked to select a group of sensory stimuli not specifically related to the user (smells, sounds, pictures, text, tastes, touch sensation, heat sensation, etc. . . . ) out of a series of stimuli.

Figure 2:
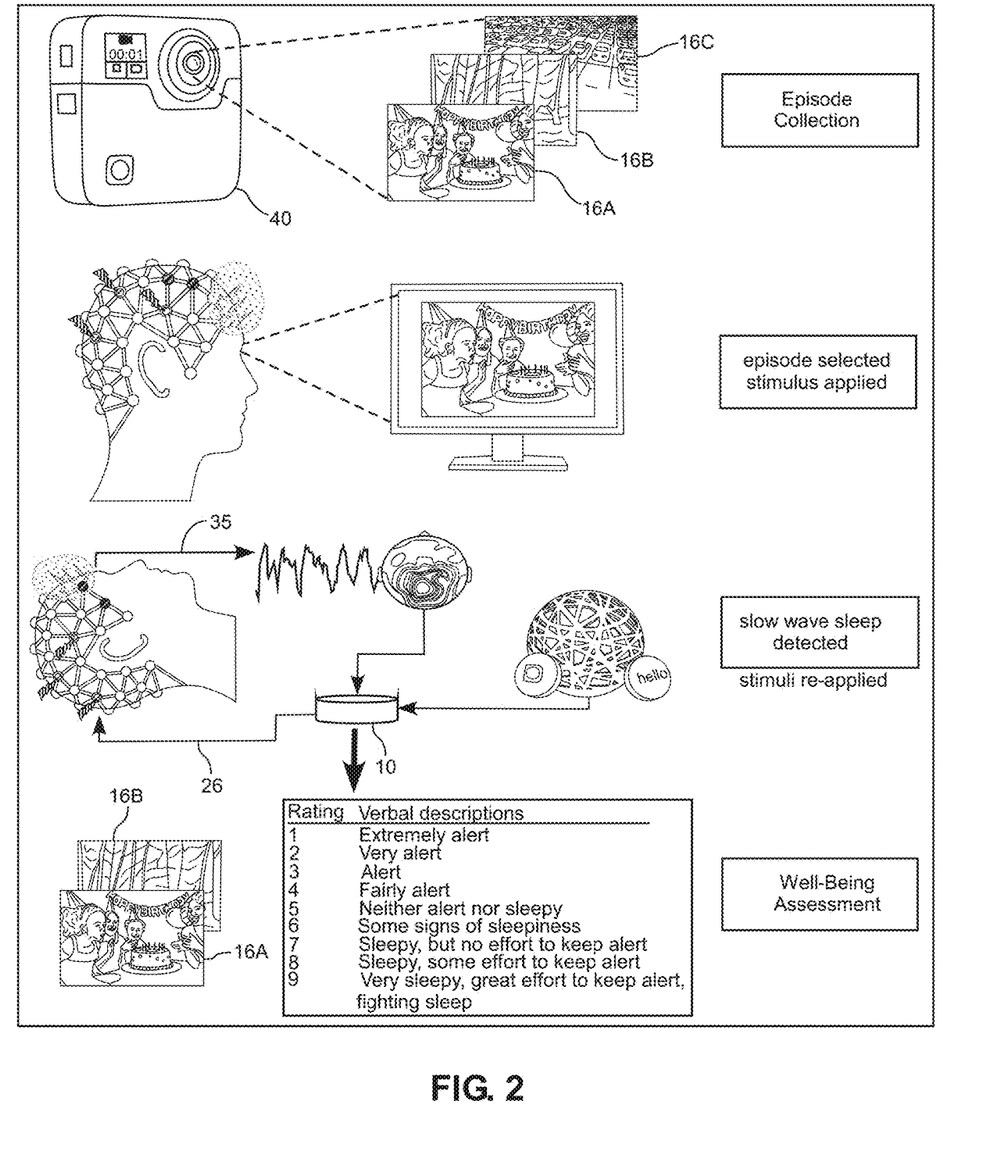
FIG. 2 illustrates the operation of a system according to embodiments of this presentation.

FIG. 2 illustrates that a system according to an embodiment of this presentation can use video episodes (16A, 16B, 16C) of personal life events as sensory stimuli, in which case a user can wear a video recording device 40 throughout the day—potentially a device similar to those known commercially under the name of "SenseCam" or "Google Glass"— that would collect a record of episodes. As detailed hereafter, in FIG. 2, first, episodes during the user's day are captured with a wearable camera device. Segments of these episodes are uploaded to a cognitive task (e.g. a task of labeling the uploaded episodes). Second, the user interacts with the cognitive task, receiving STAMPs while viewing episodes. Third, the user sleeps and receives STAMPs to cue reactivation of memories, and sleep is monitored. Fourth, the user tests their memory and sleep quality for well-being assessment.

According to an embodiment of this presentation, excerpts from the records made throughout the day can be automatically extracted based on computational measures of salience or other methods such as facial recognition or keyframe selection, and uploaded to the cognitive task to cue the user. According to an embodiment of this presentation, in case the events are selected by salience, an online salience-based detection of events can immediately alert the user to allow a unique sensory stimulus/STAMP to be applied (e.g., by pressing a button) until the end of the event. Alternatively, an online salience-based detection of events can immediately alert the user interface 12 to allow the unique sensory stimulus/STAMP to be applied to the user. Alternatively, the user may review the video records and select excerpts to be used for cuing. This can be useful for selection of less obviously salient events, or more mundane facts, such as the location of a particular building. Finally, there may be episodes or information the user wishes to remember that may not have been recorded in video—for instance, an upcoming appointment or birthday—and for these situations a text cue can be provided. While the text cues may not be as effective as video excerpts, they will provide a stimulus that can be tagged with a sensory stimulus/STAMP and cued later during sleep, and thus still provide some benefit to memory. Selected video excerpts and personal text cues can be provided to system 10 offline, whereas automatically extracted episodes can be uploaded to system 10 without user input.

According to an embodiment of this presentation, and as outlined in FIG. 2 the system 10 can further be provided for re-displaying the selected episodes (16A, 16B) to the user, for example after his sleep, and asking questions to the user, for example if the user recognizes the episodes. The system can then, for example, assess the well-being of the user based on the rate of recognition of the selected episodes.

Figure 3:
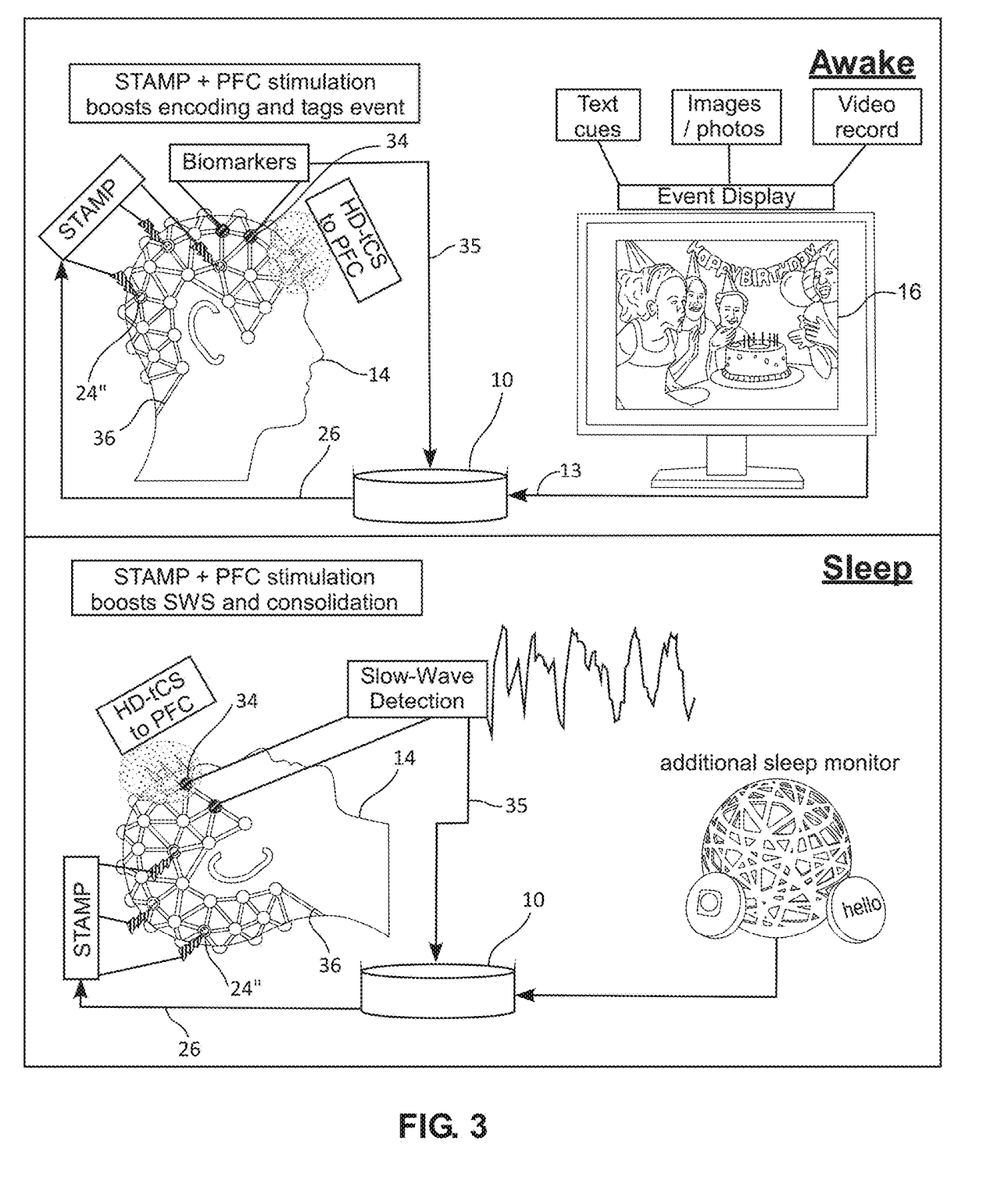
FIG. 3 illustrates the operation of a system according to embodiments of this presentation.

FIG. 3 illustrates the operation of a system according to embodiments of this presentation. As detailed hereafter, during the day (top), the user reviews episodic events 16 while receiving neurostimulation 26 to enhance encoding and tag the event. Biomarkers 35 ("biomarkers" and "neurophysiological data" should be taken to be equivalent, for the purposes of this presentation) are sent to the recording device to fine-tune the system. During the night (bottom), the user receives stimulation during upstates of slow-wave sleep to boost sleep and memory. A sleep monitor provides additional information to fine-tune the system. In the top portion of FIG. 3, user 14 wears an unobtrusive sensor suite unit (e.g., headgear 36) with combined neural sensors 34 and stimulation electrodes 24". Neurophysiological sensors 34 can be of a type that measures electrophysiological activity (EEG sensors, for example); however, other types of sensors, such as fNIRS or other technologies, could potentially be used for sensors 34. Importantly, system 10 is geared toward usage with older adults and MCI patients, and thus accessibility is a priority. Preferably, system 10 comprises both recording and stimulation units, and is easily put on and removed, and is compact, having only the channels necessary for optimal stimulation and recording. According to an embodiment of this presentation, headgear 36 comprises a 64-channel EEG cap; however, such a device can be found be overbearing and uncomfortable. Accordingly, in another embodiment of this presentation, headgear 34 comprises a dry electrode headband system. The user wears the headgear during two "phases" of the memory: a "tagging" phase and a "cueing" phase. During the tagging phase (cognitive task, illustrated in the upper part of FIG. 3) episodic memories can be tagged with STAMP neurostimulation patterns, and during sleep following the cognitive task, in the cueing phase (illustrated in the lower part of FIG. 3), the neurostimulation patterns 26 that were applied during the cognitive task are re-applied to accelerate consolidation and improve sleep quality.

The neurostimulation patterns 26 delivered to the user 14 can be in a form such as described in U.S. application Ser. No. 15/332,787. Such stimulation consists of non-invasive stimulation to the prefrontal cortex (PFC) to strengthen memory formation during the encoding task and boost slow wave oscillatory activity and memory consolidation during sleep, combined with a unique SpatioTemporal Amplitude-Modulated Pattern (STAMP) of stimulation to tag and cue memories. The specifics of a STAMP process are described in greater detail in U.S. application Ser. No. 15/332,787, but briefly, each STAMP is a spatiotemporally distributed pattern of electrical stimulation across the scalp for a brief period of time. The STAMPs are determined to be unique through a gradient descent optimization process, and are low-amplitude in nature, with the total positive current set to be under 2.5 mA, and each individual channel's current under 1.5 mA and over 150 uA. Note that while embodiments of this presentation utilize high-definition transcranial stimulation (HD-tCS) for delivery of electrical currents to the brain, other embodiments can utilize other technologies for delivery of associative cues, such as transcranial magnetic stimulation (TMS) or focused ultrasound stimulation (fUS). Each episode is assigned a unique STAMP, so that re-application will specifically cue the associated memory and not other memories.

The cognitive task can be implemented with a simple-to-use interface 12, such as for example a Graphical User Interface (GUI) that allows the user 14 to select between studying episodes, adding cues, and testing their memory. The cues provided during study can be in the form of excerpts from previously recorded videos, or alternatively text cues input by the user that describe an event or memory. User interface 12 can be arranged for associating the cues to each of the selected sensory stimuli, either automatically or upon user input. According to an embodiment of this presentation, each cue can be presented 13 on a display to user 14, and a unique STAMP current can be delivered during cue presentation to associate the cue with the electrical stimulation. These STAMP currents and the associated episodes can be saved in a database so that the STAMPs can be replayed during sleep, and so that future episodes do not re-use the same STAMP currents. This database can be accessible by the user, so that episodes considered to be obsolete or not necessary to cue can be removed.

Theoretically, providing neurostimulation when the user 14 is first experiencing or encoding an episode would provide maximal association between the episode and the STAMP; however, this is not an ideal scenario for older adults and MCI patients, as it would require wearing the stimulation device essentially at all times, which could lead to discomfort and disengagement with the device. Additionally, it is not always possible to know when exactly an episode the user will want to remember is going to occur, and thus knowing when exactly to stimulate in real-time is difficult. According to an embodiment of this presentation, this problem is not critical, as cueing memories leads to reactivation of the same neural patterns that were present at first encoding, and causes the memory to enter a more biologically active and labile state in which new information can be associated with it. Thus, cueing retrieval of memories using a system according to embodiments of this presentation serves as a reliable proxy for stimulating at the time of the events occurring.

As detailed above, STAMPs (26A, 26B) originally applied during the step of studying and encoding of certain memories during the day are re-applied during sleep to promote specific neural replays and aid consolidation. The neuroscientific theory of how this method works is outlined in greater detail in U.S. application Ser. No. 15/332,787 but briefly, neurons that previously encoded information into a memory are reactivated during specific periods of sleep, and if this memory was associated with an external stimulus, then re-presenting that stimulus during sleep will increase the likelihood of those neurons reactivating. This leads to greater consolidation of the specific reactivated memory, and thus less forgetting over time. This is particularly important for older adults, as they have reduced memory reactivations during sleep, so boosting this process can greatly improve quality of life.

An important aspect of embodiments of this presentation is a closed-loop control system, that automatically triggers onset of stimulation during upstates of slow-wave sleep based on an evaluation of the spectral power of the neurophysiological data from the user, wherein the evaluation is performed automatically (such as described in more detail in U.S. application Ser. No. 15/947,733. Neural reactivations primarily occur during up-states of the slow-wave, so targeting these time-points for STAMP stimulation is critical for boosting memory consolidation.

For a brief description of the closed-loop stimulation algorithm, the power of EEG activity in the slow wave band (0.5-1.5 Hz) is compared to power in other frequency bands, and if this ratio crosses a threshold (of e.g. 0.3) signifying the presence of detectable slow wave power, then a sine wave with the same dominant slow-wave frequency is fit to the slow-wave oscillation. The next upcoming upstate is predicted by projecting the sine wave into the future and stimulating when the phase of the wave is 0, which is the up-state. This closed-loop stimulation system has been successfully used in HRL research projects. Further, embodiments of this presentation can expand on its capabilities by tracking physiological biomarkers of successful consolidation and sleep quality, and modulating stimulation based on these parameters.

The Inventors have determined that specific changes in brain activity following stimulation—namely, changes in overall spindle band amplitude (12-15 Hz), as well as changes in beta band connectivity (16-30 Hz)—are predictive of successful memory consolidation. Thus, embodiments of a system according to this presentation will track these biomarkers following each STAMP stimulation to determine the success of stimulation, and modulate stimulation levels accordingly. For instance, if no biomarker change is detected after each application for several applications of a particular STAMP, the STAMP will be discontinued in favor of other STAMPs that are more effective in producing optimal brain changes. Additionally, the automatic closed-loop slow-wave stimulation system can be combined with other sleep sensing and physiological monitoring systems—for example, a system similar to the system known by the commercial name of "Sense" by Hello or "Beddit" by Smart 3—to track the user's sleep quality and provide adjustments to the stimulation system to maximize benefits to sleep. For instance, by tracking the user's heart rate and respiration rate, the system can stimulate during periods of restlessness or elevated arousal to improve sleep quality while still producing memory benefits. By jointly optimizing biomarker increase and sleep quality metrics, the closed-loop system can maximize memory and sleep quality benefits.

To examine the performance of the system in improving the user's episodic memory, the user can engage in a post-sleep cognitive test of their memory for the events that were cued previously. This step can be optional to the user—if desired, the user 14 could simply study episodes before the night and receive stimulation during the night. However, the user will then only be relying on his sense of whether his memory and sleep quality is improving, as opposed to having data to assess. Additionally, the STAMP stimulation system can be further optimized, and the long-term change in performance of the user can be better tracked, if the user 14 tests his memory for the events. The memory test can take many forms, and one skilled in the art can experiment with different manifestations to produce optimal results. In one simple form, the episodes that were previously studied and associated with STAMPs are also given labels or text descriptions, either automatically or by the user, and during the test the user must generate these labels based on a given episodic cue.

For episodes generated by automatic segmentation of personal video data, test cues can be developed by extracting important keyframes that are representative of the video episode.

For additional performance increases, electrophysiological biomarkers of successful or unsuccessful encoding, or brainstates associated with good memory, can be monitored to fine-tune the stimulation parameters and personalize the system for the individual.

A system 10 according to embodiments of this presentation can be arranged for, after stimulation of the user's brain during sleep (via its user interface 12):
  providing again the selected sensory stimuli (e.g., video episodes 16A, 16B) to the user 14;
  prompting the user 14 to recognize and enter the cue associated to each stimulus; and
  recording if said cue is recognized or not by user 14.

According to embodiments of this presentation, the controller 28, which receives the neurophysiological data 35 recorded for each brain stimulus, can be arranged for associating said recorded neurophysiological data 35 with the record of the cue of the brain stimulus being recognized by the user, or being not recognized by the user. Controller 28 can then be arranged for providing user 14 with a further series of sensory stimuli (e.g., new video episodes) and allowing user 14 to select a further group of selected sensory stimuli out of said further series of sensory stimuli (e.g., new selected video episodes), while having the neurophysiological data sensors 34 detect and record further neurophysiological data 35 from the user's brain when stimulated by each of said further group of brain stimuli. At this juncture, if the further neurophysiological data 35, detected when the user's brain is stimulated by at least one stimulus 26 of said further group of brain stimuli, is recognized by controller 28 as having been associated to a record of the user not recognizing a cue, controller 28 causes the stimulator to additionally stimulate the brain of user 14 with said at least one stimulus 26 of said further group of brain stimuli.

Figure 4:
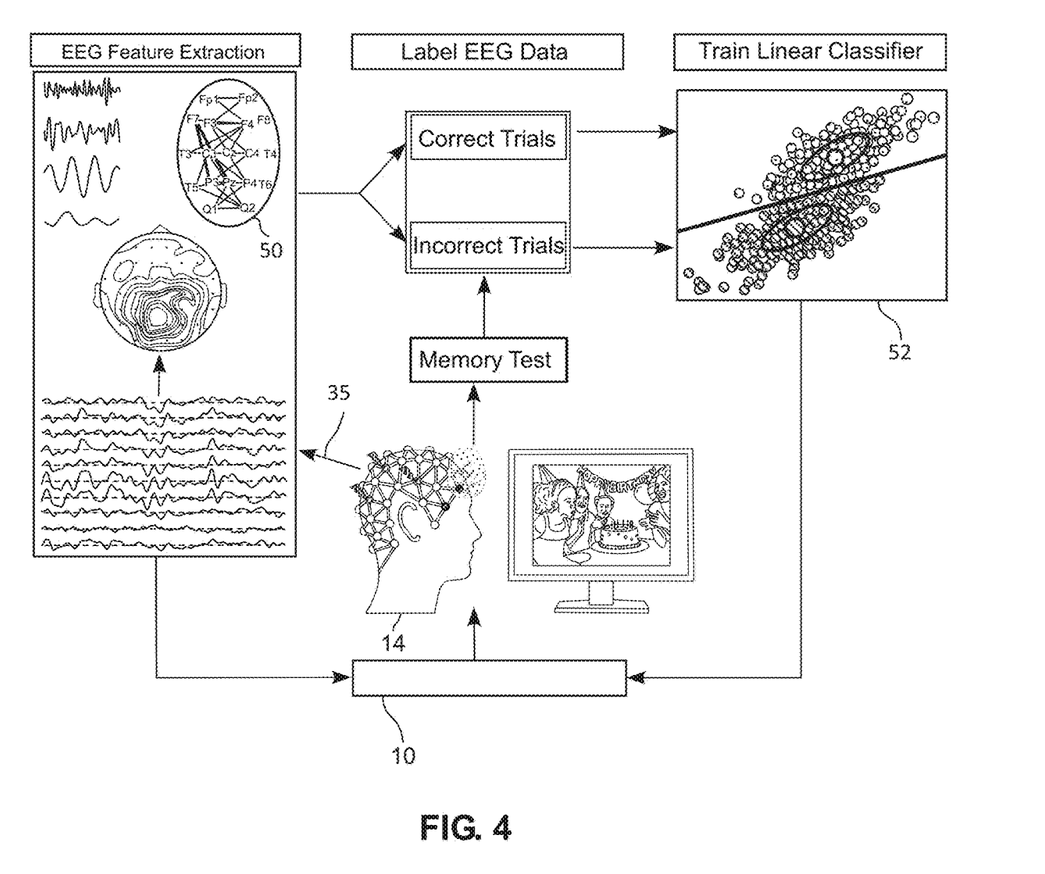
FIG. 4 illustrates the operation of a system according to embodiments of this presentation.

FIG. 4 illustrates a system 10 according to an embodiment of this presentation, provided for a more difficult and fine-grained test, where the video episode neurophysiological data 35 can be analyzed with a neural network 50 (e.g., a convolutional neural network combined with a recurrent neural network) to extract labels for detected objects, and where test cues can be generated based on these more specific object labels. The user's performance on this cognitive test can be automatically scored and used to further refine the closed-loop stimulation algorithm. As detailed hereafter, EEG features 35 are first extracted from the user as they encode information. Later, the user takes a memory test, which allows labelling of previously encoded episodes as correctly or incorrectly recalled. The EEG features 35 are grouped into these two classes, and a linear classifier is trained to separate them. During the next encoding period, EEG features 35 are classified online to determine if the user will correctly remember the episode in the future, and STAMP stimulation is modulated accordingly.

According to an embodiment of this presentation, the system 10 can require user 14 to test his memory, following sleep stimulation, and can be provided to assign labels ("correct trial"; "incorrect trial") to events/episodes during encoding that were later either remembered or forgotten. Numerous features of the electrophysiological data 35, including power in multiple frequency bands and coherence across channels and frequencies, can then be extracted and associated to "later remembered" or "later forgotten" episodes. A linear classifier 52 can be trained to separate these classes based on the neural data from the neural network 50. Then, during the next memory encoding period, the ongoing EEG data 35 would be decomposed into the same features as before and submitted to the trained linear classifier in real-time, which would inform the system whether the user is likely to remember this information or not. In this way, episodes that are unlikely to be remembered can be prioritized for STAMPing, and potentially repeated multiple times by the system until the EEG data 35 is classified such that the individual is now likely to remember the information.

Alternatively, there may be certain STAMP currents 26 that are more effective at promoting memory consolidation for each user, and so the system can select certain STAMP currents 26 based on the output of the classifier to maximize performance. This system can be continuously optimized for the user as long as the user takes memory tests to provide labeled data, as biomarkers may subtly change over time, necessitating changing the linear classifier accordingly.

To determine the performance and the success of the stimulation system in improving the user's sleep, the neurophysiological data 35 during sleep, combined with data from any other sleep sensing system, will be automatically scored by the system 10 to assess the user's sleep quality. This scoring can include amount of slow wave sleep, number of sleep spindles, heart rate and respiration rate, time spent in different sleep stages, and other important measures. This automatic physiological assessment can be combined with subjective self-assessments, such as the Pittsburgh sleep quality index [see for example "*Psychometric evaluation of the Pittsburgh sleep quality index*", by Carpenter, J. S., & Andrykowski, M. A. (1998); Journal of Psychosomatic Research, 45(1), 5-13] or the Karolinska sleepiness scale, completed by the user in order to generate a more complete profile of the user's quality of sleep. The continually updated profile of the user's sleep will be sent to the stimulation system, such that the closed-loop algorithm for stimulation will be adapted to the individual.

For instance, if stimulation during certain times of the night or with certain STAMPs leads to greater improvement of sleep quality, then the system 10 can automatically adjust to accommodate this. Additionally, clinical assessments of development of MCI symptoms can be sent to the system 10 as well so that the closed-loop system can be optimized to reduce symptoms and impede progress toward development of neurodegenerative disease. In this way, the system 10 can be personalized to the user and can be tuned continually to provide maximal enhancement and efficacy over time.

Figure 5:
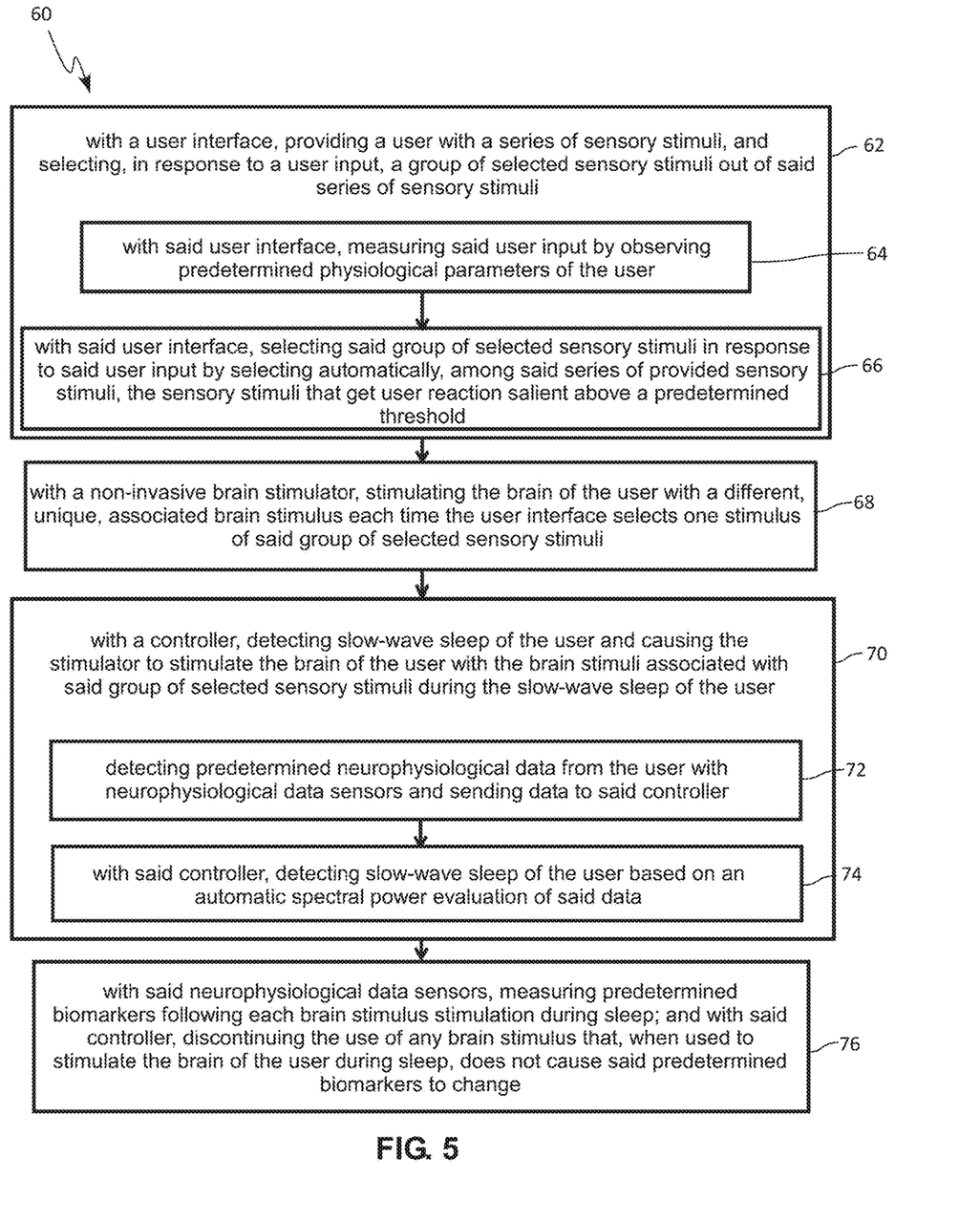
FIG. 5 illustrates a method according to embodiments of this presentation.

FIG. 5 illustrates a method 60 of neuro stimulation according to an embodiment of this presentation, the method comprising:

62 with a user interface, providing a user with a series of sensory stimuli, and selecting, in response to a user input, a group of selected sensory stimuli out of said series of sensory stimuli. According to an embodiment of this presentation, said selecting can comprise: 64 with said user interface, measuring said user input by observing predetermined physiological parameters of the user; and 66 with said user interface, selecting said group of selected sensory stimuli in response to said user input by selecting automatically, among said series of provided sensory stimuli, the sensory stimuli in response to which the user interface can sense a user reaction having a value above a predetermined threshold value.

According to an embodiment of this presentation, the method further comprises 68: with a non-invasive brain stimulator, stimulating the brain of the user with a different, unique, associated brain stimulus each time the user interface selects one stimulus of said group of selected sensory stimuli; and 70 with a controller, detecting slow-wave sleep of the user and causing the stimulator to stimulate the brain of the user with the brain stimuli associated with said group of selected sensory stimuli during the slow-wave sleep of the user.

According to an embodiment of this presentation, said detecting slow-wave sleep can comprise: 72 detecting predetermined neurophysiological data from the user with neurophysiological data sensors and sending said data to said controller; and 74: with said controller, detecting slow-wave sleep of the user based on an evaluation of the spectral power of said data, wherein the evaluation is performed automatically.

Optionally, the method further comprises 76: with said neurophysiological data sensors, measuring predetermined biomarkers following each brain stimulus stimulation during sleep; and with said controller, discontinuing the use of any brain stimulus that, when used to stimulate the brain of the user during sleep, does not cause said predetermined biomarkers to change.

Figure 6:
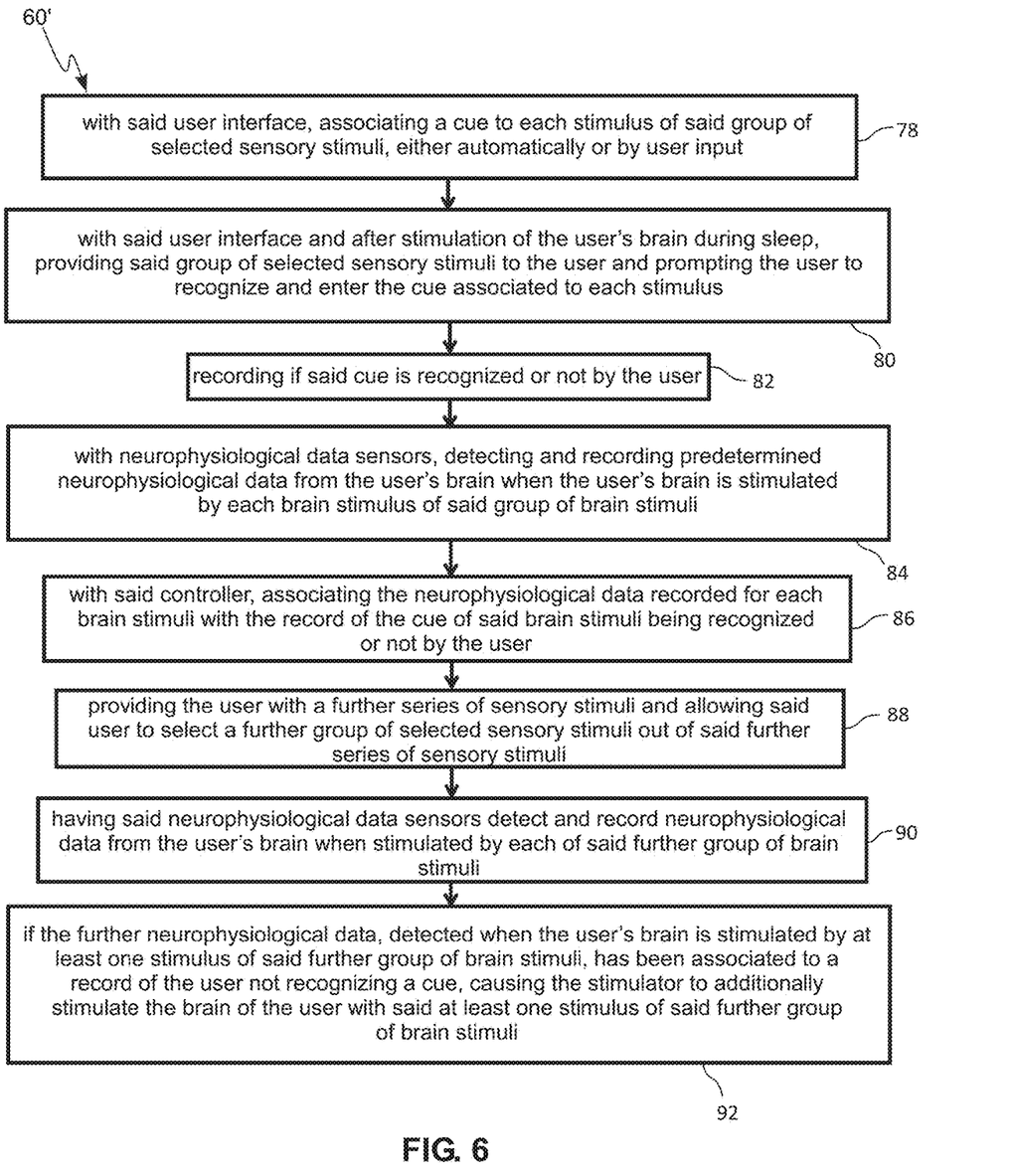
FIG. 6 illustrates a method according to embodiments of this presentation.

FIG. 6 illustrate further details 60' of the method 60 of FIG. 5. According to an embodiment of this presentation, the method 60 further comprises 78 with the user interface, associating a cue to each stimulus of the group of selected sensory stimuli, either automatically or by user input; then 80 with the user interface and after stimulation of the user's brain during sleep, providing said group of selected sensory stimuli to the user and prompting the user to recognize and enter the cue associated to each stimulus; and 82 recording if said cue is recognized or not by the user.

According to an embodiment of this presentation, the method further comprises: 84 with neurophysiological data sensors, detecting and recording predetermined neurophysiological data from the user's brain when the user's brain is stimulated by each brain stimulus of said group of brain stimuli; 86 with said controller, associating the neurophysiological data recorded for each brain stimuli with the record of the cue of said brain stimuli being recognized or not by the user; 88 providing the user with a further series of sensory stimuli and allowing said user to select a further group of selected sensory stimuli out of said further series of sensory stimuli; 90 having said neurophysiological data sensors detect and record further neurophysiological data from the user's brain when stimulated by each of said further group of brain stimuli; and 92 if the further neurophysiological data, detected when the user's brain is stimulated by at least one stimulus of said further group of brain stimuli, has been associated to a record of the user not recognizing a cue, causing the stimulator to additionally stimulate the brain of the user with said at least one stimulus of said further group of brain stimuli.

Having now described the invention in accordance with the requirements of the patent statutes, those skilled in this art will understand how to make changes and modifications to the present invention to meet their specific requirements or conditions. Such changes and modifications may be made without departing from the scope and spirit of the invention as disclosed herein.

The foregoing Detailed Description of exemplary and preferred embodiments is presented for purposes of illustration and disclosure in accordance with the requirements of the law. It is not intended to be exhaustive nor to limit the invention to the precise form(s) described, but only to enable others skilled in the art to understand how the invention may be suited for a particular use or implementation. The possibility of modifications and variations will be apparent to practitioners skilled in the art. No limitation is intended by the description of exemplary embodiments which may have included tolerances, feature dimensions, specific operating conditions, engineering specifications, or the like, and which may vary between implementations or with changes to the state of the art, and no limitation should be implied therefrom.

Applicant has made this disclosure with respect to the current state of the art, but also contemplates advancements and that adaptations in the future may take into consideration of those advancements, namely in accordance with the then current state of the art. It is intended that the scope of the invention be defined by the Claims as written and equivalents as applicable. Reference to a claim element in the singular is not intended to mean "one and only one" unless explicitly so stated. Moreover, no element, component, nor method or process step in this disclosure is intended to be dedicated to the public regardless of whether the element, component, or step is explicitly recited in the Claims. No claim element herein is to be construed under the provisions of 35 U.S.C. Sec. 112, sixth paragraph, unless the element is expressly recited using the phrase "means for . . . " and no method or process step herein is to be construed under those provisions unless the step, or steps, are expressly recited using the phrase" comprising the step (s) of . . . ."

All elements, parts and steps described herein are preferably included. It is to be understood that any of these elements, parts and steps may be replaced by other elements, parts and steps or deleted altogether as will be obvious to those skilled in the art.

The invention claimed is:

1. A neuro-stimulation system comprising:
a user interface arranged for providing a user with a series of sensory stimuli, and for selecting, in response to a user input a group of selected sensory stimuli out of said series of sensory stimuli;
a non-invasive brain stimulator arranged for stimulating the brain of the user with a different, unique, associated brain stimulus each time the user interface selects one stimulus of said group of selected sensory stimuli; and
a controller arranged for detecting slow-wave sleep of the user and for causing the stimulator to stimulate again the brain of the user, during the slow-wave sleep of the user, with each of said different, unique, associated brain stimulus that was used to stimulate the brain of the user each time the user interface selected one stimulus of said group of selected sensory stimuli;
wherein said user interface is arranged for measuring said user input by observing predetermined physiological parameters of the user; and
said user interface is arranged for selecting said group of selected sensory stimuli in response to said user input by selecting automatically, among said series of provided sensory stimuli, the sensory stimuli in response to which the user interface can sense a user reaction having a value above a predetermined threshold value.

2. The neuro-stimulation system of claim 1, wherein each brain stimulus comprises a non-invasive stimulation to the prefrontal cortex.

3. The neuro-stimulation system of claim 1, wherein each brain stimulus comprises a spatiotemporal amplitude modulated pattern comprising a pattern of electrical stimulations spatially distributed across the scalp, where the stimulations oscillate at a predetermined frequency for a predetermined period of time.

4. The neuro-stimulation system of claim 1, wherein each sensory stimulus comprises a video of events experienced by said user.

5. The neuro-stimulation system of claim 1, further comprising neurophysiological data sensors arranged for detecting predetermined neurophysiological data from the user and sending said data to said controller; wherein said controller is arranged for detecting slow-wave sleep of the user based on an evaluation of the spectral power of said data, wherein the evaluation is performed automatically.

6. The neuro-stimulation system of claim 5, wherein said neurophysiological data sensors are arranged for measuring predetermined biomarkers following each brain stimulus stimulation during sleep and wherein said controller is provided for discontinuing the use of any brain stimulus that, when used to stimulate the brain of the user during sleep, does not cause said predetermined biomarkers to change in a desired manner.

7. The neuro-stimulation system of claim 6, wherein said neurophysiological data sensors and said non-invasive brain stimulator are arranged on a headgear adapted to be worn by the user.

8. The neuro-stimulation system of claim 1, wherein said controller is arranged for tracking the user's heart rate and respiration rate, and for additionally stimulating the user's brain with the brain stimuli associated with said group of selected sensory stimuli during periods of restlessness or elevated arousal.

9. The neuro-stimulation system of claim 1, wherein said user interface is arranged for associating a cue to each stimulus of said group of selected sensory stimuli, either automatically or by user input.

10. The neuro-stimulation system of claim 9, wherein said user interface is arranged for, after stimulation of the user's brain during sleep: providing said group of selected sensory stimuli to the user; prompting the user to recognize and enter the cue associated to each stimulus; and recording if said cue is recognized or not by the user.

11. The neuro-stimulation system of claim 9, wherein the neuro-stimulation system comprises neurophysiological data sensors arranged for detecting and recording predetermined neurophysiological data from the user's brain when said user is stimulated by each of said group of brain stimuli; the controller being further arranged for:
associating the neurophysiological data recorded for each brain stimuli with the record of the cue of the brain stimuli being recognized or not by the user;
providing the user with a further series of sensory stimuli and allowing said user to select a further group of selected sensory stimuli out of said further series of sensory stimuli;
having the neurophysiological data sensors detect and record further neurophysiological data from the user's brain when stimulated by each of said further group of brain stimuli; and
if the further neurophysiological data, detected when the user's brain is stimulated by at least one stimulus of said further group of brain stimuli, has been associated to a record of the user not recognizing a cue, causing the stimulator to additionally stimulate the brain of the user with said at least one stimulus of said further group of brain stimuli.

12. The neuro-stimulation system of claim 11, wherein said neurophysiological data sensors and said non-invasive brain stimulator are arranged on a headgear to be worn by the user.

13. The neuro-stimulation system of claim 11, wherein said neurophysiological data sensors comprise an electroencephalogram recording device.

14. A neuro-stimulation method comprising:
with a user interface, providing a user with a series of sensory stimuli, measuring a user input by observing predetermined physiological parameters of the user; and
selecting automatically, among said series of provided sensory stimuli, the sensory stimuli in response to which the user interface can sense a user input having a value above a predetermined threshold value;
the method further comprising:
with a non-invasive brain stimulator, stimulating the brain of the user with a different, unique, associated brain stimulus each time the user interface selects one stimulus of said group of selected sensory stimuli; and
with a controller, detecting slow-wave sleep of the user and causing the stimulator to stimulate again the brain of the user, during the slow-wave sleep of the user, with each of said different, unique, associated brain stimulus that was used to stimulate the brain of the user each time the user interface selected one stimulus of said group of selected sensory stimuli.

15. The neuro-stimulation method of claim 14, wherein each brain stimulus comprises a non-invasive stimulation to the prefrontal cortex.

16. The neuro-stimulation method of claim 14, wherein each brain stimulus comprises a spatiotemporal amplitude modulated pattern that includes a pattern of electrical stimulations spatially distributed across the scalp, where the stimulations oscillate at a predetermined frequency for a predetermined period of time.

17. The neuro-stimulation method of claim 14, wherein each sensory stimulus comprises a video of events experienced by said user.

18. The neuro-stimulation method of claim 15, comprising:
  detecting predetermined neurophysiological data from the user with neurophysiological data sensors;
  sending said data to said controller; and,
  with said controller, detecting slow-wave sleep of the user based on an evaluation of the spectral power of said data, wherein the evaluation is performed automatically.

19. The neuro-stimulation method of claim 18, comprising:
  with said neurophysiological data sensors, measuring predetermined biomarkers following each brain stimulus stimulation during sleep; and
  with said controller, discontinuing the use of any brain stimulus that, when used to stimulate the brain of the user during sleep, does not cause said predetermined biomarkers to change.

20. The neuro-stimulation method of claim 14 comprising, with said controller, tracking the user's heart rate and respiration rate, and additionally stimulating the user's brain with the brain stimuli associated with said group of selected sensory stimuli during periods of restlessness or elevated arousal.

21. The neuro-stimulation method of claim 14 comprising, with said user interface, associating a cue to each stimulus of said group of selected sensory stimuli, either automatically or by user input.

22. The neuro-stimulation method of claim 21 comprising:
  with said user interface and after stimulation of the user's brain during sleep, providing said group of selected sensory stimuli to the user and prompting the user to recognize and enter the cue associated to each stimulus; and
  recording if said cue is recognized or not by the user.

23. The neuro-stimulation method of claim 22 comprising:
  with neurophysiological data sensors, detecting and recording predetermined neurophysiological data from the user's brain when the user's brain is stimulated by each brain stimulus of said group of brain stimuli;
  with said controller, associating the neurophysiological data recorded for each brain stimuli with the record of the cue of said brain stimuli being recognized or not by the user;
  providing the user with a further series of sensory stimuli and allowing said user to select a further group of selected sensory stimuli out of said further series of sensory stimuli;
  having said neurophysiological data sensors detect and record further neurophysiological data from the user's brain when stimulated by each of said further group of brain stimuli; and
  if the further neurophysiological data, detected when the user's brain is stimulated by at least one stimulus of said further group of brain stimuli, has been associated to a record of the user not recognizing a cue, causing the stimulator to additionally stimulate the brain of the user with said at least one stimulus of said further group of brain stimuli.

24. A neuro-stimulation system comprising:
  a user interface arranged for providing a user with a series of sensory stimuli, and for selecting, in response to a user input a group of selected sensory stimuli out of said series of sensory stimuli;
  a non-invasive brain stimulator arranged for stimulating the brain of the user with a different, unique, associated brain stimulus each time the user interface selects one stimulus of said group of selected sensory stimuli; and
  a controller arranged for detecting slow-wave sleep of the user and for causing the stimulator to stimulate again the brain of the user, during the slow-wave sleep of the user, with each of said different, unique, associated brain stimulus that was used to stimulate the brain of the user each time the user interface selected one stimulus of said group of selected sensory stimuli.

* * * * *